US012731385B2

(12) United States Patent
Greenhalgh

(10) Patent No.: US 12,731,385 B2
(45) Date of Patent: Sep. 8, 2026

(54) QUALIFICATION OF A DERMASCOPE IMAGING DEVICE

(71) Applicant: Skin Analytics Ltd., London (GB)

(72) Inventor: Jack Hector Greenhalgh, London (GB)

(73) Assignee: Skin Analytics Ltd., London (GB)

( * ) Notice: Subject to any disclaimer, the term of this patent is extended or adjusted under 35 U.S.C. 154(b) by 0 days.

(21) Appl. No.: 18/865,667

(22) PCT Filed: Jun. 7, 2023

(86) PCT No.: PCT/EP2023/065292
§ 371 (c)(1),
(2) Date: Nov. 13, 2024

(87) PCT Pub. No.: WO2024/002649
PCT Pub. Date: Jan. 4, 2024

(65) Prior Publication Data

US 2025/0308222 A1 Oct. 2, 2025

(30) Foreign Application Priority Data

Jun. 30, 2022 (GB) ..................................... 2209631

(51) Int. Cl.
*G06V 10/776* (2022.01)
*A61B 5/00* (2006.01)
(Continued)

(52) U.S. Cl.
CPC .......... *G06V 10/776* (2022.01); *A61B 5/0077* (2013.01); *A61B 5/444* (2013.01);
(Continued)

(58) Field of Classification Search
CPC ... A61B 5/0077; G01J 5/0265; G06V 10/764; G06V 10/82; G06V 10/776; G06N 20/00;
(Continued)

(56) References Cited

U.S. PATENT DOCUMENTS 5,760,829 A 6/1998 Sussmeier
2015/0065803 A1* 3/2015 Douglas .................. G06T 7/143
600/200

(Continued)

FOREIGN PATENT DOCUMENTS

GB 2461996 A 1/2010
WO WO-2021231614 A1 * 11/2021 ............. G16B 40/20

OTHER PUBLICATIONS

Veronese et al., Diagnostics, The Role in Teledermoscopy of an Inexpensive and Easy-to-Use Smartphone Device for the Classification of Three Types of Skin Lesions Using Convolutional Neural Networks, Mar. 5, 2021 (Year: 2021).*

(Continued)

*Primary Examiner* — Gerald Johnson
(74) *Attorney, Agent, or Firm* — Stoel Rives LLP

(57) ABSTRACT

Qualifying an unqualified dermascope imaging device for use with an image classification algorithm is described. A qualification data set comprising a plurality of pairs of images of skin lesions is accessed, wherein each pair comprises an image of a skin lesion captured by an unqualified dermascope imaging device and an image of the skin lesion captured by a qualified dermascope imaging device. Using the image classification algorithm, a confidence value of classification of each image is computed. A similarity metric is measured between the unqualified and qualified dermascope imaging device using differences in the confidence values between images of each pair. Qualifying the unqualified dermascope imaging device for use with the image classification algorithm is done in response a comparison between the similarity metric and a similarity threshold.

18 Claims, 3 Drawing Sheets

(51) Int. Cl.
*G06V 10/74* (2022.01)
*G06V 10/764* (2022.01)

(52) U.S. Cl.
CPC .......... *G06V 10/761* (2022.01); *G06V 10/764* (2022.01); *A61B 2560/0233* (2013.01); *G06V 2201/03* (2022.01)

(58) Field of Classification Search
CPC ........ G06N 3/0464; G06N 3/08; G06N 3/094; G06N 3/0475
See application file for complete search history.

(56) References Cited

U.S. PATENT DOCUMENTS

2020/0372638 A1* 11/2020 Gregson ................ G06V 10/82
2022/0133215 A1* 5/2022 Mayer .................... G16H 30/40 600/477
2022/0359062 A1* 11/2022 Dunn ..................... G16H 30/40
2023/0152598 A1* 5/2023 Brebner ............. G02B 27/0977 359/627

OTHER PUBLICATIONS

Alves et al., Sensors, Automatic Focus Assessment on Dermoscopic Images Acquired with Smartphones, Nov. 14, 2019 (Year: 2019).*
International Search Report and Written Opinion for PCT Application PCT/EP2023/065292 dated Sep. 12, 2023, 10 pages.
Cugmas, Blaz , et al., "Color constancy in dermatoscopy with smartphone", Progress in Biomedical Optics and Imaging, SPIE—International Society for Optical Engineering, Bellingham, WA, US, vol. 10592,, Dec. 7, 2017, pp. 1-6.

* cited by examiner

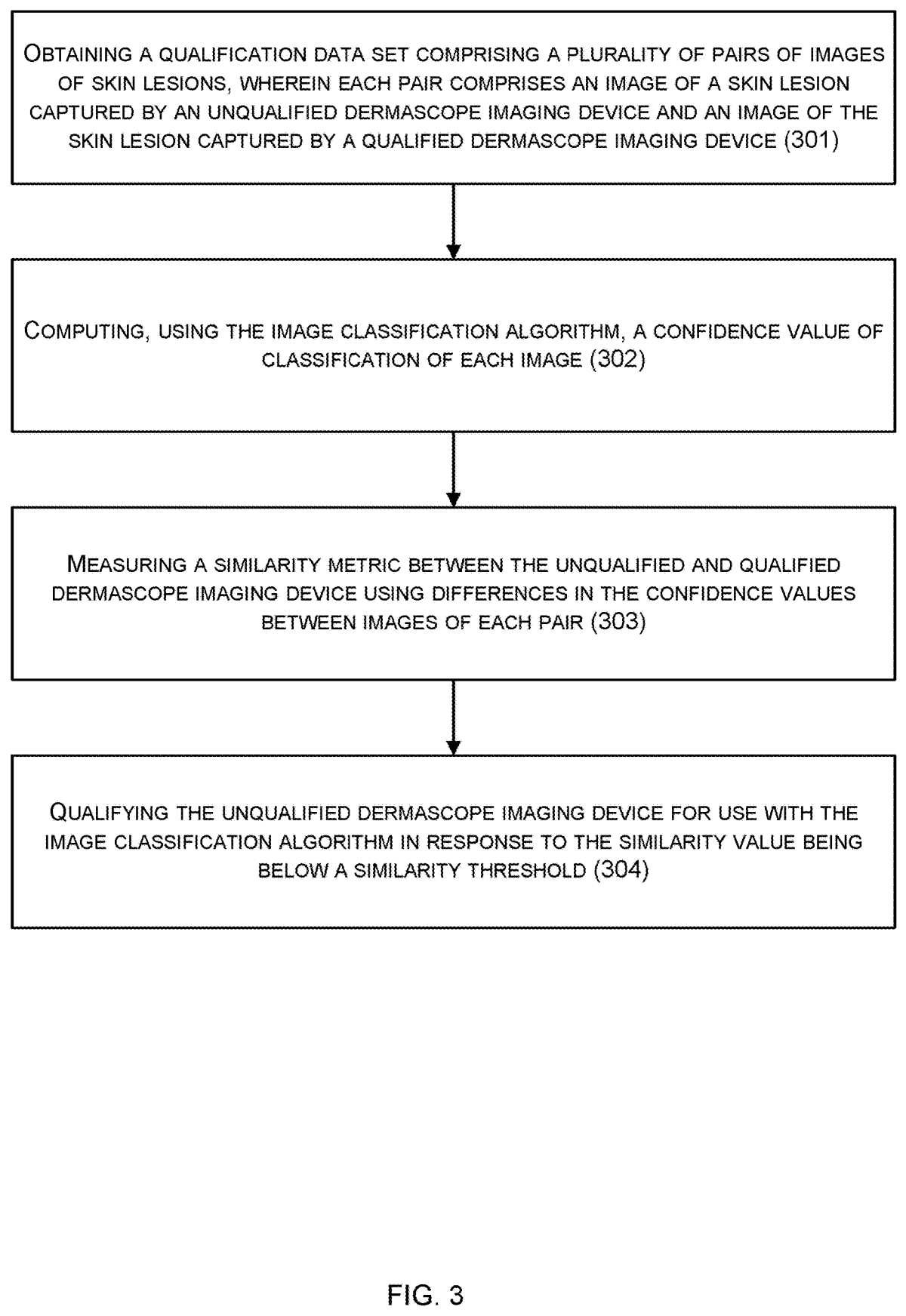

OBTAINING A QUALIFICATION DATA SET COMPRISING A PLURALITY OF PAIRS OF IMAGES OF SKIN LESIONS, WHEREIN EACH PAIR COMPRISES AN IMAGE OF A SKIN LESION CAPTURED BY AN UNQUALIFIED DERMASCOPE IMAGING DEVICE AND AN IMAGE OF THE SKIN LESION CAPTURED BY A QUALIFIED DERMASCOPE IMAGING DEVICE (301)

↓

COMPUTING, USING THE IMAGE CLASSIFICATION ALGORITHM, A CONFIDENCE VALUE OF CLASSIFICATION OF EACH IMAGE (302)

↓

MEASURING A SIMILARITY METRIC BETWEEN THE UNQUALIFIED AND QUALIFIED DERMASCOPE IMAGING DEVICE USING DIFFERENCES IN THE CONFIDENCE VALUES BETWEEN IMAGES OF EACH PAIR (303)

↓

QUALIFYING THE UNQUALIFIED DERMASCOPE IMAGING DEVICE FOR USE WITH THE IMAGE CLASSIFICATION ALGORITHM IN RESPONSE TO THE SIMILARITY VALUE BEING BELOW A SIMILARITY THRESHOLD (304)

FIG. 3

QUALIFICATION OF A DERMASCOPE IMAGING DEVICE

This application is a U.S. National Stage of PCT application No. PCT/EP2023/065292 filed on Jun. 7, 2023, which claims priority to GB application No. 2209631.7, filed on Jun. 30, 2022, the contents of which are hereby incorporated by reference in their entirety for any purpose.

BACKGROUND

Dermoscopy, also known as dermatoscopy, is a form of skin surface microscopy, often used in skin cancer diagnosis and, more generally, the examination of skin lesions. A dermascope, also known as a dermatoscope, is an instrument used to perform dermoscopy; the dermascope comprises a magnifier and a light source (polarized or non-polarized). A dermascope can be attached to an image-capture device (such as a digital camera or a smartphone), and a captured image of a skin lesion, by the image-capture device combined with the dermascope, is processed using an algorithm to distinguish between benign and malignant lesions.

SUMMARY

The following presents a simplified summary of the disclosure in order to provide a basic understanding to the reader. This summary is not intended to identify key features or essential features of the claimed subject matter nor is it intended to be used to limit the scope of the claimed subject matter. Its sole purpose is to present a selection of concepts disclosed herein in a simplified form as a prelude to the more detailed description that is presented later.

Disclosed herein is a computer-implemented method for qualifying an unqualified dermascope imaging device for use with an image classification algorithm, the method comprising the steps of: obtaining a qualification data set comprising a plurality of pairs of images of skin lesions, wherein each pair comprises an image of a skin lesion captured by an unqualified dermascope imaging device and an image of the skin lesion captured by a qualified dermascope imaging device; computing, using the image classification algorithm, a confidence value of classification of each image; measuring a similarity metric between the unqualified and qualified dermascope imaging device using differences in the confidence values between images of each pair; and qualifying the unqualified dermascope imaging device for use with the image classification algorithm in response to a comparison between the similarity metric and a similarity threshold.

DESCRIPTION OF THE DRAWINGS

The present description will be better understood from the following detailed description read in light of the accompanying drawings, wherein:

FIG. 3 is a block diagram relating to an example method for qualifying an unqualified dermascope imaging device for use with an image classification algorithm.

DETAILED DESCRIPTION

Figure 1:
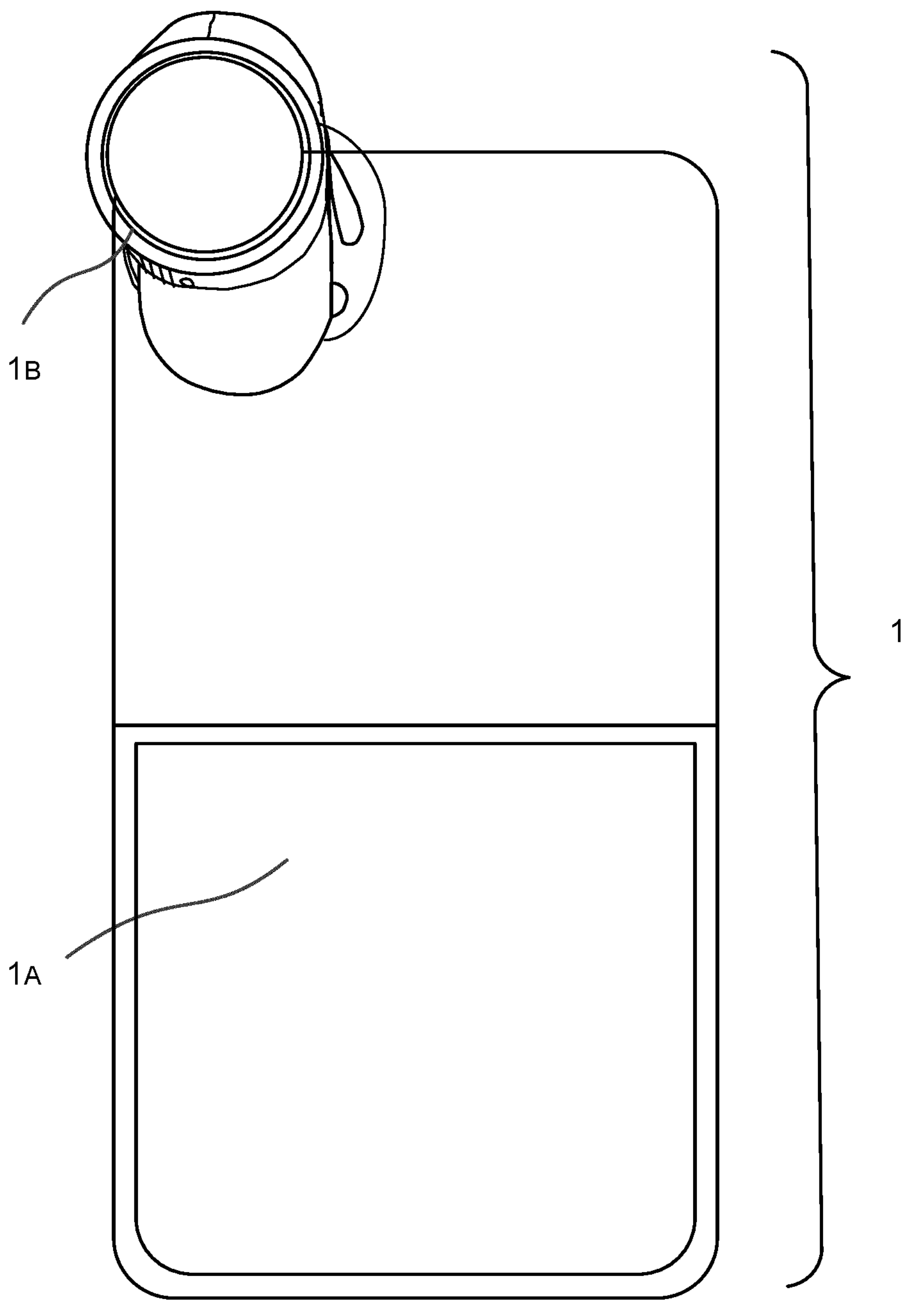
FIG. 1 is a schematic diagram of an example dermascope imaging device.

The detailed description provided below in connection with the appended drawings is intended as a description of the present examples and is not intended to represent the only forms in which the present examples are constructed or utilized. The description sets forth the functions of the examples and the sequence of operations for constructing and operating the examples. However, the same or equivalent functions and sequences may be accomplished by different examples.

The present technology is concerned with qualifying an image-capture device with a particular dermascope. A dermascope, also known as a dermatoscope, is an instrument used to perform dermoscopy, the dermascope comprises a magnifier and a light source (polarized or non-polarized). A dermascope can be attached to an image-capture device, and a captured image of a skin lesion, by the image-capture device combined with the dermascope, is processed using an algorithm to distinguish between benign and malignant lesions. An image-capture device combined with a dermascope is referred to as dermascope imaging device.

The term "qualifying" is used to refer to validating an image-capture device to be operable with a dermascope and specified image processing algorithm. The term "image-capture device" is used to refer to any device with an optical instrument to capture images, e.g. a digital camera, a hand-held smartphone, a tablet computer or other image-capture device.

At present, the most common approach for qualifying a dermascope imaging device is to validate said dermascope imaging device using a prospective clinical study. This is both costly and very time-consuming, and also uses up considerable resources of the health services. Given the rate at which new image-capture devices, such as smartphones, are released or image-capture device software is updated, and the impracticality of running a prospective study for every new image-capture device to be qualified, an improved method to qualify an image-capture device in combination with a dermascope (i.e. a dermascope imaging device) has been developed.

In order for a dermascope imaging device to be regarded as qualified, running a classification algorithm (e.g. a malignant/benign skin classification algorithm) on the "unqualified" dermascope imaging device produces similar predictions for a particular lesion or skin patch to a reference device. A reference device is a "qualified" dermascope imaging device which is known to reliably operate with the classification algorithm. The predictions can be quantified in terms of confidence values assigned to each captured image of a skin lesion. For example, a lesion with a confidence value of 0.6 for 'benign melanocytic nevus', 0.1 for 'solar lentigo', and 0.3 for 'seborrheic keratosis' for one dermascope imaging device should produce similar confidence scores when captured with another dermascope imaging device. If this is not the case, the dermascope imaging device is unsuitable for use with the classification algorithm.

The inventors have recognized that there is enough variation between benign lesions captured from the general population to ensure that if the assertion (similar confidence scores regardless of capture device) holds for an unqualified dermascope imaging device with respect to a reference device, the unqualified dermascope imaging device can be qualified for use with the classification algorithm.

There are several examples of the types of variation which can be observed between the captured images of different dermascope imaging devices, such as variations in white balance, variations in image resolution, proprietary post-processing (including blurring and sharpening of the image), differences in cross-polarised light emitting diodes LEDs used in the dermascope, variations in magnification used in the dermascope and/or de-mosaicking algorithms. If a classification algorithm produces similar confidence values for two different capture devices, the sensitivity and specificity of classifying the lesions will also be similar, regardless of the variations between capture devices.

FIG. 1 shows an image-capture device 1*a* attached to a dermascope 1*b*, i.e. a dermascope imaging device 1. In some examples, the image-capture device 1*a* comprises a dermascope 1*b*, i.e. they are formed as a single device.

A metric, the mean confidence distance (MCD), has been defined by the inventors which is calculated to define whether a dermascope imaging device is suitable for use with the classification algorithm. A method for determining the threshold to be applied to the MCD metric in order to qualify a new dermascope imaging device has also been defined by the inventors.

TABLE 1

Breakdown of lesion type numbers for an Exemplary Threshold Calibration Data Set

| Category | Lesion Type | Number | Percentage of Total (%) |
|---|---|---|---|
| Malignant | Melanoma | 117 | 2.59 |
| | SCC | 90 | 1.99 |
| | BCC | 262 | 5.80 |
| Premalignant | IEC | 185 | 4.1 |
| | AK | 549 | 12.16 |
| Atypical | Atypical Nevus | 291 | 6.45 |
| Benign | Benign Vascular Lesion | 115 | 2.55 |
| | Seborrheic Keratosis | 1177 | 26.07 |
| | Dermatofibroma | 79 | 1.75 |
| | Solar Lentigo | 65 | 1.44 |
| | Benign Melanocytic Nevus | 725 | 16.06 |
| | Benign | 860 | 19.05 |
| | TOTAL | 4515 | 100 |

Table 1 describes an exemplary data set used to develop the dermascope imaging device qualification method and calculate the MCD upper threshold. The MCD upper threshold is used to determine whether a dermascope imaging device has passed device qualification. The exemplary data described in Table 1 was collected empirically with appropriate consents.

The labels for the lesions in Table 1 were provided by the exemplary sources as described in Table 2, with malignant (Melanoma, Squamous Cell Carcinoma (SCC) and Basal Cell Carcinoma (BCC)) lesions confirmed by histopathology.

TABLE 2

Breakdown of source of ground-truth for an Exemplary Threshold Calibration Data Set

| Label source | Number | Percentage of Total (%) |
|---|---|---|
| Histopathology | 1243 | 27.53 |
| Face-to-face dermatology | 1982 | 43.9 |
| Teledermatology | 1290 | 28.57 |
| TOTAL | 4515 | 100 |

The qualification method compares images by using the predicted confidence values from a layer of a neural network of a machine learning based classification algorithm, e.g. the final layer of the neural network of the machine learning based classification algorithm. Other layers, such as the penultimate layer, or any other layer of the neural network, can alternatively or additionally be used.

To compare images of the same lesion from two capture devices (wherein one of the devices is a reference device which is already known to be operable with the classification algorithm), a matrix of confidence values is calculated for each image in a pair of images and the mean squared error (MSE) between the matrices is found. The MSE is calculated between image pairs for the two dermascope imaging devices (i.e. the unqualified dermascope imaging device and the qualified reference device), and the mean MSE over all the possible pairs calculated. This metric, referred to as the mean confidence distance (MCD), is a single value, which describes the similarity of the response of a classification algorithm for two devices.

The MCD is defined as follows:

$$MCD(A, B) = \frac{\sum_{j=0}^{K} \sum_{i=0}^{N} |A_{(i,j)} - B_{(i,j)}|^2}{N \times K}$$

where A and B are matrices comprising confidence values for lesions for capture device A and B, respectively, i is the confidence for a lesion type, j is a specific lesion in the data set, N is the total number of lesion types, and K is the total number of lesions. The value of K, the total number of lesions, can be any number less than 1000, and in some scenarios between 100 and 200, e.g. 120. Two devices with a MCD below a pre-defined threshold can be assumed to give similar sensitivity and specificity in terms of a classification task. The above equation for the mean confidence distance is expressed in words as: the average mean squared difference between the confidence values of image ij from capture device A and image ij from capture device B. The confidence values of image ij are given in matrix format since there is one confidence value per predicted lesion type output by the classification algorithm, and one set of confidence values per image.

As an alternative to calculating the MCD (i.e. the similarity metric), or in addition to, the reciprocal of the dot product between the confidence values for each of the reference device and the unqualified device can be calculated as the similarity metric (instead of the mean square error). In another alternative to calculating the MCD as the similarity metric, the Cross Entropy Loss between the confidence values for each of the reference device and the unqualified device can be calculated, rather than the mean square error. Although the MCD metric is referred to throughout this application, the skilled person would understand that the alternatives mentioned could also be used as the similarity metric instead of the MCD metric.

In order for a dermascope imaging device to be regarded as qualified, the similarity metric between the dermascope imaging device and the reference device (qualified imaging device) is lower or equal to a predetermined threshold.

One method for determining the MCD threshold (i.e. the similarity threshold) involves first acquiring a statistically significant number of biopsy-labelled lesion images from a large number of dermascope imaging devices, including malignant, premalignant and benign lesion types. Each lesion is captured using a variety of dermascope imaging devices, ideally of varying image quality. Gathering a real-world data set of this nature would be impractical, time consuming, expensive and difficult. A more practical approach is to synthesise this data set by applying a set of distortions and/or transformations to a data set of images from a single dermascope imaging device, to simulate multiple dermascope imaging devices.

Confidence values are found for the subset of lesions in the exemplary Threshold Calibration Data Set (Table 2) that are labelled by teledermatology. In table 2, this includes 1290 images. Typically, this subset of captured images is expected to comprise of mostly or all "clearly benign" lesions whereby a face-to-face specialist appointment or biopsy is not required. Therefore, these lesions are similar to the lesions used to perform dermascope imaging device qualification (as a user performing these is unlikely to have access to non-benign lesions).

A series of parameterised distortions/transformations are applied to the captured images, using randomised (or otherwise) parameter values, and the similarity metric is calculated between the distorted and non-distorted images. These distortions/transformations may include any one or more of the following: Scaling of a red RGB colour channel, Scaling of a green RGB colour channel, Scaling of a blue RGB colour channel, Randomised down-sampling (reducing the size of the image, and then resizing to the original size), Randomised cropping (where the crop size is randomised), Randomised rotation (where the angle of rotation is randomised), Randomised blurring (where the size of the Gaussian kernel used to blur is randomised). Other distortions/transformations may include any of the following: Addition of randomised noise to the pixel values of the image, Image translation (whereby the pixels are shifted vertically, horizontally or diagonally) use of a generative adversarial network (GAN/CycleGAN) to generate images which appear to be captured using a different capture device. The term distortion includes transformations as well as distortions, i.e. any alteration of the captured image.

The artificial distortions/transformations are applied to the captured images to simulate dermascope imaging devices of varying quality. The inventors have recognized that a reason why this works effectively when used in the device qualification method is that if the classification algorithm (e.g. machine-learning classification algorithm) gives a different confidence value for a particular dermascope imaging device compared to a reference device, the performance of that particular dermascope imaging device is likely to also be different. Therefore, dermascope imaging devices that are inappropriate for the purpose of reliably and accurately identifying lesions when paired with a dermascope can be detected without needing to know exactly why or how the captured images vary.

Figure 2:
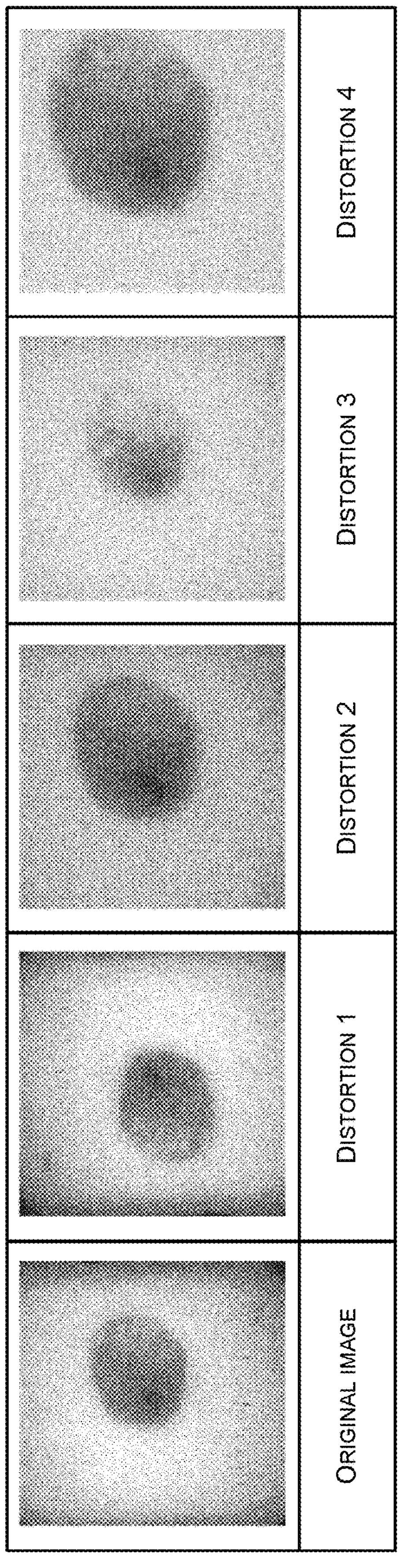
FIG. 2 is a schematic representation of distortions and/or transformations applied to an image of a skin lesion.

FIG. 2 shows various distortions applied to the same lesion image. The process of applying distortions/transformations is repeated for a number of iterations (e.g. 100 iterations). In some examples, for every iteration, each distortion/transformation is applied once. As seen in FIG. 2, four iterations of applying distortions/transformations are shown (Distortion 1-Distortion 4).

The images labelled by teledermatology are distorted using identical distortions parameters (at each iteration). Therefore, in some examples, every image will have the green RGB channel scaled by the same random value. The confidence values for these distorted images are then found via the classification algorithm, and the similarity metric is calculated between the distorted and original, non-distorted images. Table 3 shows the similarity values for each of the exemplary distortions from FIG. 2:

TABLE 3

Mean confidence distance (MCD) values achieved for the 'teledermatology discharge' lesions from exemplary Threshold Calibration data set, calculated for the original image and 4 sets of distortions.

| | No Distortion | Distortion 1 | Distortion 2 | Distortion 3 | Distortion 4 |
|---|---|---|---|---|---|
| Similarity values | 0.0 | 0.000697 | 0.014212 | 0.015993 | 0.008338 |

It can be seen in Table 3 that the severely distorted image in Distortion 3 (as seen in FIG. 2) provides the highest similarity value whereas the least distorted image (Distortion 1) provides the lowest similarity value.

At each iteration, the same parameterized distortions are applied to at least some (or all) of the remaining images in the exemplary threshold calibration data set (which comprises images labelled by histopathology and teledermatology). The exemplary data set comprises histologically confirmed malignant and premalignant lesions, and histologically and clinically confirmed benign lesions. The same randomised parameters as before are used to distort these reference images, and the area under the receiver operator characteristic curve (AUROC) is found for each malignant and premalignant lesion type, as 'one-against-all' (e.g. melanoma vs non-melanoma, basal cell carcinoma bcc vs non-bcc etc.). Alternatives to this metric could also be used, including sensitivity, specificity, or accuracy.

The AUROCs for each malignant and premalignant lesion type are found for the original, non-distorted data set, along with the confidence intervals at, for example, 95% (the confidence intervals can be calculated using bootstrapping with replacement).

The MCD and AUROC for each lesion is recorded for each simulated dermascope imaging device, for a total of, for example, 100 simulated dermascope imaging devices. These values are then sorted by MCD in ascending order, and the largest MCD before any AUROC drops below its lower confidence interval is taken as the MCD Threshold used, i.e. the predetermined MCD threshold. Table 4 shows the AUROCs achieved on this exemplary data set after the distortions shown in FIG. 2 have been applied.

TABLE 4

Area under receiver operator characteristic (AUROC) curve for each lesion type, for non-distorted and distorted images created using 4 different sets of distortion parameters

| | Non Distorted | Distortion 1 | Distortion 2 | Distortion 3 | Distortion 4 |
|---|---|---|---|---|---|
| MCD | 0.0 | 0.000697 | 0.014212 | 0.015993 | 0.008338 |
| Melanoma AUROC (%) | 92.52 | 92.22 | 91.06 | 84.85 | 86.01 |
| SCC AUROC (%) | 89.75 | 89.77 | 86.94 | 81.86 | 83.64 |
| BCC AUROC (%) | 94.38 | 94.54 | 92.08 | 78.56 | 81.05 |
| IEC AUROC (%) | 81.97 | 81.76 | 82.9 | 72.70 | 68.20 |
| AK AUROC (%) | 87.20 | 87.30 | 84.78 | 78.73 | 74.26 |

By running the classification algorithm described above on the exemplary data set, an MCD threshold of 0.005871 is produced. At this level, the AUROC scores for the lesions are within this range. The next highest MCD was '0.006270', which was still within range for the lesion types apart from 'BCC', for which the AUROC was '93.05%' (less than the lower bound of 93.38%). The AUROC scores for this data are shown in Table 5, along with the acceptable AUROC ranges.

TABLE 5

Area under receiver operator characteristic (AUROC) curve for each lesion type, for non-distorted images and the distorted images used to determine the mean confidence distance (MCD) threshold (AUROC value with is out of range is marked in boldface).

| Lesion Type | AUROC for non-distorted images (with confidence intervals at 95%) (%) | AUROC for distorted images used to set threshold settings (MCD = 0.005871) (%) | AUROC for distorted images with lowest MCD to drop out of AUROC range (MCD = 0.006370)(%) |
|---|---|---|---|
| Melanoma | 92.52 (90.44 to 94.17) | 92.28 | 91.83 |
| SCC | 89.75 (87.23 to 92.21) | 88.96 | 89.45 |
| BCC | 94.38 (93.38 to 95.40) | 93.93 | **93.05** |
| IEC | 81.97 (79.49 to 84.23) | 83.18 | 82.54 |
| AK | 87.20 (86.02 to 88.36) | 86.80 | 87.30 |

Based on the exemplary data set, any unqualified dermascope imaging device which produces an MCD less than the predetermined threshold of 0.005871 (when compared to the reference device) has passed the device qualification and is, therefore, regarded as a qualified dermascope imaging device that is operable with the same classification algorithm and dermascope as the reference device.

To apply the dermascope imaging device qualification method, a new data set of lesion images is collected. The data set comprises a plurality (e.g. 120) of images of skin lesions captured using a reference dermascope imaging device (e.g. Apple iphone (trade mark) with DL1 (trade mark) basic dermascope), and a plurality of images (ideally the same number as the number of images taken by the reference device) of the same skin lesions captured with the dermascope imaging device to be qualified. An advantage of the present invention is that there is no need for the collected data set of lesion images to include malignant lesions, any lesions will do, whether they are malignant or benign—this means a human expert is not required to look through the captured images.

The solution of the present invention has the benefit of being quicker, more practical and cheaper than running an entire prospective study to qualify a new image-capture device.

The present application discloses, as shown in FIG. 3, a computer-implemented method for qualifying an unqualified dermascope imaging device for use with an image classification algorithm, the method comprising the steps of: obtaining 301 a qualification data set comprising a plurality of pairs of images of skin lesions, wherein each pair comprises an image of a skin lesion captured by an unqualified dermascope imaging device and an image of the skin lesion captured by a qualified dermascope imaging device; computing 302, using the image classification algorithm, a confidence value of classification of each image; measuring 303 a similarity metric between the unqualified and qualified dermascope imaging device using differences in the confidence values between images of each pair; qualifying 304 the unqualified dermascope imaging device for use with the image classification algorithm in response to the similarity value being below a similarity threshold.

In some examples, the similarity threshold is calculated by: obtaining a calibration data set of skin lesion images where the confidence value of each image is known and wherein each skin lesion image is labelled as a lesion type comprising any of: malignant, premalignant, benign; applying a same series of parameterised distortions and/or transformations to each image from the calibration data set; computing, using a classification algorithm, a confidence value of a classification of each image of the distorted and/or transformed images; measuring the similarity metric between each image of the calibration data set and each corresponding distorted/transformed image; determining a receiver operator curve, AUROC, for each skin lesion image of type malignant and premaligant, the AUROC having a confidence interval; recording the similarity metric and AUROC for each pair comprising a calibration image and a distorted/transformed image; selecting the largest similarity metric before any AUROC drops below its confidence interval as the similarity threshold. This way of computing the similarity threshold is found to give reliable and accurate results when the similarity threshold is used as part of the process for qualifying image capture devices. It is unexpectedly found that distorting/transforming the images gives a high quality similarity threshold and means that it is not necessary to obtain empirical images from vast numbers of labelled images of skin lesions obtained from different image capture devices. Various different similarity metrics are usable such as mean squared difference, dot product, cross entropy loss.

In some examples, the similarity metric is equal to $$MCD(A, B) = \frac{\sum_{j=0}^{K} \sum_{i=0}^{N} |A_{(i,j)} - B_{(i,j)}|^2}{N \times K},$$

which is a mean squared difference between A and B over all the images, where A is a matrix of the confidence values for all images from the qualified capture device, B is a matrix of the confidence values for all images from the unqualified capture device (or vice versa), i is a confidence associated with a lesion type, j is a specific lesion image in the calibration data set, N is the total number of lesion types, and K is the total number of lesion image pairs. Using this similarity metric with the mean squared difference is found to be efficient to compute and to give high quality results in practice.

In some examples, the distortions and/or transformations comprise any of: scaling of a red RGB colour channel, scaling of a green RGB colour channel, scaling of a blue RGB colour channel, randomised down-sampling, randomised cropping, randomised rotation, randomised blurring, addition of randomised noise to the pixel values of the image, image translation and/or use of a generative adversarial network (GAN/CycleGAN) to generate images which appear to be captured using a different capture device. In the case of scaling of a colour channel, the image capture device is a colour image capture device with a plurality of colour channels. Each of these ways of computing the distortions and/or transformations is found to be effective and give high quality results despite the fact that in many of these cases significant information is lost so that it may have been assumed the process would not work.

In some examples, each pair of images of a skin lesion captured by an unqualified dermascope imaging device and by a qualified dermascope imaging device are of lesion type benign. This is a significant benefit as obtaining images of benign skin lesions is much more straightforward than for other types of skin lesion. In various examples the images captured by the unqualified dermascope imaging device are unlabelled, that is, it is unknown whether they depict benign, premalignant or malignant skin lesions.

In some examples, the confidence interval is calculated using bootstrapping with replacement. This is found to be efficient and to give effective, high quality results.

In some examples, the image classification algorithm is a machine-learning based image classification algorithm.

In some examples, the confidence value of classification of each image is calculated using a final layer of the machine-learning based image classification algorithm. Using the outputs from the final layer enables a confidence value for each image element of the image to be computed in an efficient and accurate manner. During training the machine learning image classifier has been trained to produce accurate values at the output layer and so using these accurate values is beneficial.

In alternative examples, the confidence value of classification of each image is calculated using a layer other than the final layer of the machine-learning based image classification algorithm. Using values from an earlier layer which is not the final layer improves processing speed since computation is not through all of the layers. Using values from an earlier layer is likely to give values which are less confident overall so that bigger differences between the confidence values of the image pairs are observed making the similarity metric more sensitive.

In some examples, the unqualified dermascope imaging device comprises an imaging device and a dermascope. In some examples, the imaging device is a smartphone device. These options are practical devices which are readily commercially available and operable by lay people in domestic settings.

In alternative examples, the imaging device is a DSLR camera.

In some examples, the total number of lesion images is between 100 and 200. Thus the task of obtaining the images is practical to achieve manually.

In some examples, the qualified dermascope imaging device was qualified using the above method.

The present application also discloses a dermascope imaging device comprising a processor and storage storing computer executable instructions configured to perform the above method.

The computer executable instructions are provided using any computer-readable media that is accessible by networking router. Computer-readable media includes, for example, computer storage media such as memory and communications media. Computer storage media, such as memory, includes volatile and non-volatile, removable and non-removable media implemented in any method or technology for storage of information such as computer readable instructions, data structures, program modules or the like. Computer storage media includes, but is not limited to, random access memory (RAM), read only memory (ROM), erasable programmable read only memory (EPROM), electronic erasable programmable read only memory (EEPROM), flash memory or other memory technology, compact disc read only memory (CD-ROM), digital versatile disks (DVD) or other optical storage, magnetic cassettes, magnetic tape, magnetic disk storage or other magnetic storage devices, or any other non-transmission medium that is used to store information for access by a computing device. In contrast, communication media embody computer readable instructions, data structures, program modules, or the like in a modulated data signal, such as a carrier wave, or other transport mechanism. As defined herein, computer storage media does not include communication media. Therefore, a computer storage medium should not be interpreted to be a propagating signal per se. Although the computer storage media (memory) is shown within the computing-based device it will be appreciated that the storage is, in some examples, distributed or located remotely and accessed via a network or other communication link (e.g. using communication interface).

The term 'computer' or 'computing-based device' is used herein to refer to any device with processing capability such that it executes instructions. Those skilled in the art will realize that such processing capabilities are incorporated into many different devices and therefore the terms 'computer' and 'computing-based device' each include personal computers (PCs), servers, mobile telephones (including smart phones), tablet computers, set-top boxes, media players, games consoles, personal digital assistants, wearable computers, and many other devices.

The methods described herein are performed, in some examples, by software in machine readable form on a tangible storage medium e.g. in the form of a computer program comprising computer program code means adapted to perform all the operations of one or more of the methods described herein when the program is run on a computer and where the computer program may be embodied on a computer readable medium. The software is suitable for execution on a parallel processor or a serial processor such that the method operations may be carried out in any suitable order, or simultaneously.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items.

The operations of the methods described herein may be carried out in any suitable order, or simultaneously where appropriate. Additionally, individual blocks may be deleted from any of the methods without departing from the scope of the subject matter described herein. Aspects of any of the examples described above may be combined with aspects of any of the other examples described to form further examples without losing the effect sought.

The term 'comprising' is used herein to mean including the method blocks or elements identified, but that such blocks or elements do not comprise an exclusive list and a method or apparatus may contain additional blocks or elements.

It will be understood that the above description is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this specification.

What is claimed is:

1. A computer-implemented method for qualifying an unqualified dermascope imaging device for use with an image classification algorithm, the method comprising:
- accessing a qualification data set comprising a plurality of pairs of images of skin lesions, wherein each pair comprises an image of a skin lesion captured by an unqualified dermascope imaging device and an image of the skin lesion captured by a qualified dermascope imaging device;
- computing, using the image classification algorithm, a confidence value of classification of each image, wherein the image classification algorithm is a machine-learning based image classification algorithm;
- measuring a similarity metric between the unqualified and qualified dermascope imaging devices using differences in the confidence values between images of each pair; and
- qualifying the unqualified dermascope imaging device for use with the image classification algorithm in response a comparison between the similarity metric and a similarity threshold, wherein the similarity threshold is calculated by:
  - obtaining a calibration data set of skin lesion images where a confidence value of each image computed using the image classification algorithm is known and wherein each skin lesion image is labelled as a lesion type comprising any of: malignant, premalignant, benign;
  - applying a same series of parameterised distortions and/or transformations to each image from the calibration data set;
  - computing, using the image classification algorithm, a confidence value of a classification of each image of the distorted and/or transformed images;
  - measuring the similarity metric between each image of the calibration data set and each corresponding distorted/transformed image;
  - determining a sensitivity metric for each skin lesion image of type malignant and premalignant, the sensitivity metric having a confidence interval;
  - recording the similarity metric and the sensitivity metric for each pair comprising a calibration image and a distorted/transformed image; and
  - selecting a largest similarity metric before a sensitivity metric drops below a threshold as the similarity threshold.

2. The computer-implemented method of claim 1, wherein the similarity metric is any of: a mean squared difference, a dot product, a cross entropy loss.

3. The computer-implemented method of claim 1, wherein the similarity metric is equal to $$\frac{\sum_{j=0}^{K}\sum_{i=0}^{N}|A_{(i,j)}-B_{(i,j)}|^2}{N\times K},$$

where A is a matrix of confidence values of image elements of image ij from the qualified dermascope imaging device, B is a matrix of confidence values of image elements of image ij from the unqualified dermascope imaging device, i is a confidence associated with the lesion type, j is a specific lesion image in the calibration data set, N is a total number of lesion types, and K is a total number of lesion image pairs.

4. The computer-implemented method of claim 3, wherein the total number of lesions is between 100 and 200.

5. The computer-implemented method of claim 1, wherein the distortions and/or transformations comprise any one or more of: scaling of a red RGB colour channel, scaling of a green RGB colour channel, scaling of a blue RGB colour channel, randomised down-sampling, randomised cropping, randomised rotation, randomised blurring, addition of randomised noise to the pixel values of the image, image translation, use of a generative adversarial network (GAN/CycleGAN) to generate images which appear to be captured using a different capture device.

6. The computer-implemented method of claim 1, wherein the confidence interval is calculated using bootstrapping with replacement.

7. The computer-implemented method of claim 1, wherein each pair of images are of lesion type benign.

8. The computer-implemented method of claim 1, wherein the confidence value of classification of each image is calculated using a final layer of the machine-learning based image classification algorithm.

9. The computer-implemented method of claim 1, wherein the confidence value of classification of each image is calculated using a layer other than the final layer of the machine-learning based image classification algorithm.

10. The computer-implemented method of claim 1, wherein the unqualified dermascope imaging device comprises an imaging device and a dermascope.

11. The computer-implemented method of claim 10, wherein the imaging device is a smartphone device or a digital single-lens reflex (DSLR) camera.

12. The computer-implemented method of claim 1, wherein qualifying the unqualified dermascope imaging device results in a second qualified dermascope imaging device which is used to qualify a second unqualified dermascope imaging device using the method of claim 1.

13. A dermascope imaging device comprising:
- a processor and storage, wherein the processor is configured to perform qualifying the dermascope imaging device for use with an image classification algorithm, said qualifying comprising:
  - accessing a qualification data set comprising a plurality of pairs of images of skin lesions, wherein each pair comprises an image of a skin lesion captured by an unqualified dermascope imaging device and an image of the skin lesion captured by a qualified dermascope imaging device;
  - computing, using the image classification algorithm, a confidence value of classification of each image, wherein the image classification algorithm is a machine-learning based image classification algorithm;
  - measuring a similarity metric between the unqualified and qualified dermascope imaging device using differences in the confidence values between images of each pair; and
  - qualifying the unqualified dermascope imaging device for use with the image classification algorithm in response a comparison between the similarity metric and a similarity threshold, wherein the processor is further configured to calculate the similarity threshold, performing:
  - obtaining a calibration data set of skin lesion images where a confidence value of each image computed using the image classification algorithm is known and wherein each skin lesion image is labelled as a lesion type comprising any of: malignant, premalignant, benign;

applying a same series of parameterised distortions and/or transformations to each image from the calibration data set;

computing, using the image classification algorithm, a confidence value of a classification of each image of the distorted and/or transformed images;

measuring the similarity metric between each image of the calibration data set and each corresponding distorted/transformed image;

determining a sensitivity metric for each skin lesion image of type malignant and premalignant, the sensitivity metric having a confidence interval;

recording the similarity metric and sensitivity metric for each pair comprising a calibration image and a distorted/transformed image; and selecting a largest similarity metric before any similarity metric drops below its confidence interval as the similarity threshold.

14. The computer-implemented method of claim 1, wherein a processor is configured to execute the accessing a qualification data set, computing a confidence value, measuring a similarity metric, and qualifying the unqualified dermascope imaging device.

15. The dermascope imaging device of claim 13, wherein the distortions and/or transformations comprise any one or more of: scaling of a red RGB colour channel, scaling of a green RGB colour channel, scaling of a blue RGB colour channel, randomised down-sampling, randomised cropping, randomised rotation, randomised blurring, addition of randomised noise to the pixel values of the image, image translation, use of a generative adversarial network (GAN/CycleGAN) to generate images which appear to be captured using a different capture device.

16. The dermascope imaging device of claim 13, wherein the confidence interval is calculated using bootstrapping with replacement.

17. The dermascope imaging device of claim 13, further comprising an imaging device and a dermascope.

18. The dermascope imaging device of claim 17, wherein the imaging device is a smartphone device or a digital single-lens reflex (DSLR) camera.

* * * * *